(12) United States Patent
Portillo Rosado

(10) Patent No.: US 12,151,011 B2
(45) Date of Patent: Nov. 26, 2024

(54) COMPOSITION FOR DELAYING AND DYEING GREY HAIR

(71) Applicant: Rosa Maria Portillo Rosado, Santo Domingo (DO)

(72) Inventor: Rosa Maria Portillo Rosado, Santo Domingo (DO)

( * ) Notice: Subject to any disclaimer, the term of this patent is extended or adjusted under 35 U.S.C. 154(b) by 523 days.

(21) Appl. No.: 17/753,132

(22) PCT Filed: Jun. 18, 2020

(86) PCT No.: PCT/DO2020/050003
§ 371 (c)(1),
(2) Date: Feb. 21, 2022

(87) PCT Pub. No.: WO2021/037322
PCT Pub. Date: Mar. 4, 2021

(65) Prior Publication Data
US 2022/0273544 A1    Sep. 1, 2022

(30) Foreign Application Priority Data
Aug. 27, 2019   (DM) .................................. 2019-0222

(51) Int. Cl.
| | | |
|---|---|---|
| *A61K 8/65* | (2006.01) | |
| *A61K 8/72* | (2006.01) | |
| *A61K 8/73* | (2006.01) | |
| *A61Q 5/06* | (2006.01) | |
| *A61Q 5/08* | (2006.01) | |

(52) U.S. Cl.
CPC .................. *A61K 8/65* (2013.01); *A61K 8/72* (2013.01); *A61K 8/731* (2013.01); *A61Q 5/06* (2013.01); *A61Q 5/08* (2013.01)

(58) Field of Classification Search
CPC . A61K 8/65; A61K 8/72; A61K 8/731; A61K 8/31; A61K 8/342; A61K 8/345; A61K 8/36; A61K 8/37; A61K 2800/882; A61K 8/365; A61K 8/416; A61K 8/42; A61K 8/49; A61K 8/4946; A61K 8/64; A61K 8/735; A61K 8/817; A61K 8/9794; A61Q 5/06; A61Q 5/08; A61Q 5/10
See application file for complete search history.

(56) References Cited

U.S. PATENT DOCUMENTS

| | | |
|---|---|---|
| 2003/0131425 A1 | 7/2003 | Hoeffkes |
| 2007/0041925 A1 | 2/2007 | Picano |
| 2015/0182441 A1 | 7/2015 | Goutsis |
| 2015/0209261 A1 | 7/2015 | Ross |

FOREIGN PATENT DOCUMENTS

| | | | |
|---|---|---|---|
| BR | PI1010487 | 10/2013 | |
| BR | 102014029858 | 10/2016 | |
| CA | 3067899 | 1/2019 | |
| CN | 102860977 | 1/2013 | |
| CN | 104306225 | 1/2015 | |
| CN | 105520859 | 4/2016 | |
| CN | 105832570 | 8/2016 | |
| CN | 106551834 | 4/2017 | |
| CN | 107898724 | 4/2018 | |
| CN | 107951803 | 4/2018 | |
| CN | 108721201 | 11/2018 | |
| EP | 1779838 | 5/2007 | |
| ES | 2581180 | 9/2016 | |
| GB | 2414666 A | * 12/2005 | ............. A01N 25/04 |
| JP | 2854837 | 2/1999 | |
| JP | H1143422 | 2/1999 | |
| JP | 2012158556 | 8/2012 | |
| JP | 2013053171 | 3/2013 | |
| KR | 20130081003 | 7/2013 | |
| KR | 101509608 | 4/2015 | |

OTHER PUBLICATIONS

Mintel; May 15, 2020 anonymous: Treatment XP093050284 Database accesion No. 7622147 *Ingredients; p. 2.

* cited by examiner

*Primary Examiner* — Ernst V Arnold
(74) *Attorney, Agent, or Firm* — Defillo & Associates, Inc.; Evelyn A Defillo

(57) ABSTRACT

A composition for the treatment of grey and damaged hair that contains collagen, Hydroxyethylcellulose, Polyquaternium 7, Aloe Vera, Dextropantothenyl Alcohol, Elastin Hydrolyzate, Sodium Hyaluronate, Keratin, Citric Acid, Preservative, Fragrance and Deionized Water. The composition can be formulated in aqueous form or as a cream and allows to tint and delay grey hair, restoring the natural color of the hair, activating it and forming reflections, achieving a revitalizing effect on the hair in a very short treatment time.

5 Claims, No Drawings

COMPOSITION FOR DELAYING AND DYEING GREY HAIR

CROSS REFERENCE TO RELATED APPLICATION

This application is a national stage entry of PCT/DO2020/050003 filed Jun. 18, 2020, under the International Convention and claiming priority over Dominican Republic Patent Application No. 2019-0222 filed Aug. 27, 2019.

FIELD OF THE INVENTION

The present invention relates to compositions for the treatment of grey and damaged hair and more particularly to a composition that can be formulated in aqueous or cream form that, when applied to grey and damaged hair, repairs it, and tints grey hair, activates and forms reflections in the hair, returns the natural color to the hair, and delays the appearance of grey hair, without the use of colorants or peroxides, from the appropriate conjugation of non-aggressive active ingredients, which in the appropriate amounts and upon exposure in the sun and heat, they provide a revitalizing effect on the hair in a very short treatment time, restoring the color of damaged and grey hair, giving it body and volume.

BACKGROUND OF THE INVENTION

Repairing damaged hair, avoiding the constant dyeing of grey hair, as well as reviving and fixing the natural color avoiding hair loss and volume loss, has now become one of the main aesthetic goals and challenges pursued by each day show healthier hair by eliminating dryness, fragility and dullness in the hair caused by excessive use of dyes. The main causes of this deterioration are diverse and range from those caused by the excessive use of irons and dryers, the application of inappropriate chemical products, as well as the bad habit of exposing the hair for long periods of time to the sun and poor hydration. Returning the color to hair that turns white due to the appearance of grey hair, as well as reversing the damage to the hair can be a difficult process, however, surprisingly it has been found that it is not impossible, it only requires adequate and less aggressive treatments that ensure to recover the color, strength and vitality of the hair.

At all times, around 85% of our hair is in a growth phase, known as the anagen phase, while the remaining 15% is in the resting or telogen phase, which means that it has reached its full growth potential and that it will eventually fall. This is the reason why it is completely natural for men and women to renew a small amount of hair on a day-to-day basis. Hair loss occurs when certain triggers, such as those mentioned above, disrupt the healthy growth cycle and more hair than normal enters the resting (shedding) phase, resulting in noticeable hairless areas. Due to the ever-changing nature of hormones throughout our lives, women are particularly vulnerable to some hair loss triggers attributed to hormonal change, such as pregnancy and menopause. Hair growth and color really depend on the structure and qualitative work of the hair follicle or melanocyte cells, which produce melanin. It is made up of eumelanin and pheomelanin and, depending on the amount and proportion of these pigments, the entire spectrum of hair colors that we know is obtained.

With age, or as a result of the influence of internal causes, the activity of melanin decreases and it literally stops interacting with the proteins of the hair, which is why the roots begin to turn grey. The entire bleaching process can take up to 10 years, it is impossible to completely turn grey from one moment to the next, even under very strong stress. The nerves usually only accelerate the process of deterioration of the hair structure.

Hair loss is generally thought of primarily as a male problem, primarily affecting older men. However, it has also been found that many women now face loss of hair density and body at some point in their life, which can have a negative impact on self-esteem and confidence. Hair loss in women can occur for a number of reasons, stress, diet, medication, hormonal changes, and even a hereditary predisposition for hair loss are factors that can contribute to hair thinning and loss.

It has been proven that both pregnancy and postpartum are particularly difficult times for a woman's body, and in some cases, they can cause female alopecia due to the alteration in the body's regular hormonal balance. While television and magazines tend to portray pregnancy as a phase of "radiant femininity," pregnancy-related hair loss can be a disturbing experience for women. The reason for this hair loss is an increase in estrogen and progesterone hormones, which can cause hair to become brittle and start to thin. Some women may also experience hair loss in the months following birth due to a thyroid hormone imbalance. However, there is already evidence that hair loss during and after pregnancy is usually temporary. After nine months of fluctuating hormone levels, it is normal for the body to take some time to return to its normal rhythm. Even in cases of hair loss after pregnancy, normal growth function should resume within 2 to 3 months after delivery, when hormone levels begin to stabilize.

Currently it is proven that using shampoo, conditioner and mask to meet the particular needs of each hair and guarantee its vitality is not enough. There are currently a wide variety of brands specialized in hair care on the market that have created a wide range of products to revitalize the hair that are not only designed according to the type of hair and scalp (oily, mixed, normal or dry), but also taking into account the thickness of the strand and its specific condition, that is, dyed, discolored, grey, porous, damaged or aged, developing a wide range of therapies combined with different products.

The well-known hyaluronic acid hair therapy is based on filling in the porosity due to mechanical or chemical damage. The restorative effect attributed to it, restoring the hair's resistance to withstand dyes, discolorations or abrupt changes, generally requires a combination with other ingredients, such as white clay, which controls scalp oil, and silicon, organic, to stimulate hair growth, strengthening it and preventing hair loss.

There are also hair treatments with various types of keratins, these also generally contain other chemical ingredients that are aggressive such as formaldehyde or acetic acid, the effect of the treatment lasts between four and six months. There are other alternatives also based on keratin that is less aggressive and healthier alternatives based on carbocysteine, glycoxylic acid and biotin, thus offering to add new nutrients to the hair, however the effect only lasts two months. That is why today large brands of hair treatment products and the need to ensure their vitality are involved in the development of new combinations of less toxic products, ensuring that they do not generate burning or discomfort in the eyes and nose.

The products called hair revitalizers are based on an antifrizz therapy that keeps the volume of the hair under control, they generally state that they do not contain chemicals and their composition is essentially based on the application of nutrients. Treatment includes coenzyme 010, for example, poses that strengthen the scalp; These products include argan oil, olive oil and soy lecithin, which help to provide deep nutrition, together with biotin, vitamins C, E and B2 that ensure to restore the porous fiber and make it look aligned. In this case, the treatment must end with the application of an iron to seal the benefits of the product, the effect in this case only lasts between 15 and 20 days.

The well-known nourishing ampoules are concentrates of nutrients, usually for single use, and very specific purposes are attributed to the hair, for example the duck embryo ampoules ensure to give shine and softness to the hair. Those of flax seed oil are specifically recommended to recover chemically damaged hair and those of placenta are suggested their specific application for restructuring and strengthening the hair.

The so-called dermo-cosmetic treatments are the most recent treatments to revitalize the hair and constitute one of the latest technologies and products for hair care, they are based on treatments with nutraceuticals and biological adaptogens that are generally treatments that do not have toxic ingredients and they can even be used in other parts of the body, its function specifically is to promote cell regeneration in the skin and hair, activating the communication and reproduction of cells.

There is currently a wide variety of hair treatment products on the market, which ensure through different mechanisms to stimulate its abundant and healthy growth; many of them are based on natural products as a more effective alternative to minimize the damaging effects of chemical products traditionally used for this purpose and which have been shown to be more aggressive than beneficial when used frequently in these hair treatments.

The HAIRFLUENCE product, for example, is a proposed growth formula. Its main component is biotin and it will help hair fibers grow healthily. Another of the most used ingredients in these types of products is castor oil, which they claim will help hair grow healthy and strong. Some of these products that are offered to the market are also combined with vitamins and other natural oils, which will guarantee the hydration of the scalp to provide an adequate treatment from the roots. Coconut oil, for example, is also a very common ingredient in recent times in these products for the purpose of providing a natural shine and noticeable growth.

Collagen is also recognized as an effective ingredient in the natural restoration, elasticity and hydration process of the skin, and is part of the hair structure to which it provides firmness, elasticity, body and smoothness; It also affects the blood circulation not only of the scalp but also of the hair follicle that promotes the natural pigment of the hair. Collagen constitutes a key protein for the human body in general, in fact it represents 30% of the total protein in the body and 70% of the protein in the skin; however, the natural production of collagen decreases with age, it is the amino acids and proteins contained in collagen that maintain the hair with the necessary strength and resistance, in addition to controlling its growth in a normal cycle, ensuring the cohesion of the tissues and its mechanical resistance.

The products that are currently marketed with the purpose of activating and tinting the hair are generally based on several products at the same time and function as a system where they are combined in a juxtaposition of beneficial effects of the properties of each of the ingredients; one of the main purposes sought with these ingredients is their purifying power to detoxify the hair, for example in this regard, some of these products are based on a shot of amino acids to revive the internal structure of the hair strand and the scalp; another type of product for the hair can be the so-called protectors, which generally do not require rinsing to modify and regenerate the movement and structure of the hair, gives shine, and protects against the sun's rays through the use of substances such as filters. UB, UBV and UV. Hair scrubs are also known, to remove dead cells from the scalp, this ingredient usually removes excess hair products for nutrition and restructuring that settle at the root of the hair and removes the first layer of skin, like a normal peeling, so that the follicle has new life. It is generally suggested that these products only be applied once a month.

There are other types of treatments on the market, such as the one based on the application of fluid oil, this procedure seeks to keep the effects of pollution on the hair under control and for this it is based on encapsulating the polluting particles so that they do not penetrate the hair fiber and leave silky and shiny hair. These types of products are recommended to be applied several times a day, from medium to ends. Thermal protectors are also currently used with great popularity; however, experts assure that the application is abused by the application of heat tools to the hair. The existence of fluid oils, serums, oils and styling creams is recognized, but their exclusive mission is to protect the hair from the heat emitted by the appliances, sealing the cuticle, thus allowing the product's nutrients to be activated and better penetrate. These types of products are recommended to be applied from medium to ends after drying and before using an iron, tweezers or electric brush.

In the patent information it has also been possible to identify different products based on the application of various active principles to ensure that growth is activated.

Patent CN102860977 entitled: "Liquid shampoo for damaged hair", shows a shampoo for the treatment of damaged hair that mainly comprises the following active components by mass: 0.5-5% phytochrome extraction solution, 0.8-1.2% polysiloxane-15, 0.4-0.6% sodium hyaluronate, 0.03-0.05% silk collagen, 0.03-0.05% lactoferrin, 0.03-0.05% protein emulsion complex and a suitable amount of deionized water. Silk collagen, lactoferrin and protein emulsion complex contained in shampoo liquid can strengthen hair tenacity, replenish nutrition to hair cores, and repair damaged hair. The polysiloxane-15 contained in the liquid shampoo can delay the white turn of normal hair without coloring and prematurely fade the color of the colored hair. The solution contained in the liquid shampoo has the effects of oxidation resistance, color fixation, protects hair color and improves hair shine. The hyaluronate contained in the liquid shampoo can form a film layer on the hair surfaces and has the effect of preserving moisture, greasing and protecting the hair, eliminating static electricity.

Patent CN104306225 entitled: "Nutritional hair conditioner" describes a nutritional hair conditioner that is prepared from the following raw materials in parts by weight: 5-7 parts of olive oil, 3-5 parts of seed oil green tea, 2-6 parts hazelnut oil, 2-4 parts cetostearyl alcohol, 1-3 parts lecithin, 4-6 parts coconut betaine glycine, 4-5 parts collagen, 1-2 parts of hyaluronic acid, 2-4 parts of citric acid, 1-3 parts of aloe essence, 1-3 parts of methyl 4-hydroxybenzoate, 1-3 parts of propyl 4-hydroxybenzoate, 1-3 parts of hexadecanol and 80-100 parts of refined water. The nutritional hair conditioner is gentle, does not irritate the mucous membrane of the skin, and has the effect of inhibiting bacteria, resisting static electricity and protecting the hair, so that a protective film can be formed to retain moisture in the hair and the scalp after using the conditioner can be effectively protected.

Patent CN105520859 entitled: "Dry-hair treatment oil and preparation method", describes an oil for the treatment of dry hair and a method of preparing the same. The treatment oil for dry hair is prepared from 3-10 parts of jojoba wax, 20-30 parts of cyclic dimethyl siloxane, 1-2 parts of hydrolyzed collagen protein, 1-3 parts of citric acid, 1-5 parts of polyquaternium, 2-5 parts of phenylmethyl silicone oil, 4-6 parts of essence, 1-2 parts of preservatives and 100-200 parts of distilled water. Dry hair treatment oil is capable of replenishing hair lipids and repairing damaged hairs, and excellent in regulating action.

Patent CN105832570, entitled: "Hair recombination repair liquid and preparation method thereof", refers to a hair recombination repair liquid that comprises 0.04-0.06% by weight of sodium hyaluronate, 4.5-5.5% by weight of glycerin, 2-3% by weight of hydrolyzed keratin, 1.5-2.5% by weight of hydrolyzed collagen, 0.3-1.7% by weight of pyrrolidone carboxylic acid, 0.9-1.1% by weight sodium lactate, 0.7-0.9% by weight of arginine, 0.5-0.7% by weight of aspartic acid, 0.25-0.35% by weight of pyrrolidone carboxylic acid, 0.18-0.22% by weight of glycine, 0.18-0.22% by weight alanine, 0.18-0.22% by weight of serine, 0.18-0.22% by weight of valine, 0.18-0.22% by weight of proline, 0.18-0.22% by weight of theronine, 0.18-0.22% by weight of isoleucine, 0.18-0.22% by weight of histidine and water.

Patent CN106551834 entitled: "Rose collagen restoring hair mask" describes rose collagen that restores the hair mask. A solvent is heated to the temperature of 60° C., Hydrolyzed collagen, hydrolyzed keratin, coconut dimethyl silanol hyalurate, rose extracts, palmityl alcohol, glycol distearate, cyclomethicone, dimethicone, ammonium distetanol ethyl ethoxyethyl sulfate, coconut dimethyl. Hydroxypropyl ammonium hydrolyzed keratin, provitamin B5, polyquaternium-37, perfume, phenoxyethanol, phenoxetol, stearic acid monoglycerinum, propanediol, propylene glycol, PPG-1 trideceth-6 and pigment are added. Stirring is carried out after adding each component. Cooling is carried out until the temperature is 35-40° C. Citric acid is added to adjust the pH. With the use of the rose collagen restoring the hair mask, the hair can absorb the nutrients sufficiently, and in the meantime, a protective layer is formed outside the hair, to prevent the hair from being damaged again, and the hair can be maintained soft and elastic.

Patent CN107898724 entitled: "Formula of hair conditioner", describes a formula of a hair conditioner that is prepared from the following components in parts by weight: 6 to 12 parts of sorbitol, 7 to 15 parts of polyglycerol, 8 to 12 parts of coconut oil, 4 to 8 parts of collagen, 10 to 12 parts of Vitamin A Palmitate, 12 to 15 parts of aloe gel, 11 to 17 parts of panthenol, 12 to 15 parts of lecithin, 12 to 17 parts of hexadecanol, 14 to 20 parts of octadecanol, 15 to 19 parts of emulsifier and 50 to 80 parts of deionized water. Hair conditioner has beneficial effects.

Patent CN107951803 entitled "Preparation method of hair conditioner" describes a method of preparing a hair conditioner. The preparation method comprises: sorbitol, polyglycerin, coconut oil, collagen, vitamin A palmitate, aloe gel, panthenol, lecithin, hexadecanol, octadecanol, an emulsifier and deionized water, they are prepared in parts by weight; sorbitol, olyglycerine, coconut oil, collagen, vitamin A palmitate, aloe gel, and emulsifier are evenly mixed and stirred, and an emulsified mixture is prepared; the emulsified mixture is uniformly mixed with panthenol, lecithin and hexadecanol; the mixture and octadecane are added to deionized water to preserve heat; A mixed solution cools down naturally after keeping it warm, and you get the hair conditioner.

Patent CN108721201 entitled: "Multiple-effect repair hairdressing gel and preparation method", a hairdressing gel comprises the following components: 5-8 parts of cetostearyl alcohol, 2-5 parts of octadecyl trimethyl ammonium chloride, 1-2 parts of behentrimonium chloride, 0.5-1 parts of glycerin monostearate, 1-2 parts of olive oil, 1-2 parts of wool fat, 0.8-1.2 parts of hydroxyethylcellulose, 0.05-0.1 parts of citric acid, 3-5 parts of glycerin, 2-3 parts of dimethyl silicone, 1-2 parts of panthenol, 0.3-0.5 parts of hydrolyzed collagen, 1-3 parts of *Lactobacillus plantarum*/rice yeast, 2-4 parts of a yeast extract of *Aspergillus oryzae*/rice, 3-5 parts of a TCM extract and 0.05-0.1 part of CIT/MIT. The rice washing water is fermented using *Lactobacillus plantarum* and applied to the preparation of the hairdressing gel, and the extract of traditional Chinese medicine is added, so due to the complementary and auxiliary effects of the two, it has Aiming at nourishing hair, restoring elasticity and hair blackening.

In patent JPH1143422 entitled: "HAIR COSMETIC", it discloses a hair cosmetic to treat fine hair, damaged and cut hair and to eliminate dandruff and itching of the scalp, which comprises 85-95% by weight of a chitosan obtained by deacetylation 85-95% by weight of chitin, 0.3-1.0% by weight of elastin, 1-10% by weight of placental essence, 1-10% by weight % of hyaluronic acid, 1-10% by weight of collagen and 10-60% by weight of licorice essence as a detergent component, except water, a cleaning component, and a rinse component except water, the rinse component, and a treatment component.

Patent KR20130081003 entitled: "COMPOSITION FOR HAIR TREATMENT", discloses a composition for hair treatment to minimize the damage that all kinds of chemical substances for hair dyeing cause to the scalp or hair in the dyeing or permanent procedure. (permanent wave), the hair treatment composition comprises arginine, hyaluronic acid, radix glycyrrhizal extract, vitamin C, collagen, keratin, cell membrane complex and purified water. The composition comprises 5-8% by weight of arginine, 0.01-1% by weight of hyaluronic acid, 10-15% by weight of glycixiris radixe, 0.1-1.0% by weight of vitamin C, 5-15% by weight of collagen, 5-15% by weight of keratin, 5-10% by weight of cell membrane complex, and residual purified water based on total weight.

In patent JP2012158556 referring to a protective lotion for the scalp, recommended to be used before coloring the hair to prevent hair loss, as well as reducing the appearance of grey hair, they propose a lotion obtained from soy lecithin to eliminate the human sebum that is applied to the scalp before coloring the hair to moderate the damage caused by the action of the hair coloring agent. In this case, soy lecithin is used as ingredients of the lotion together with glycerin, plant extracts, essential oils, selected from the essence of rosemary, sage, German chamomile ylang-ylang and tocopherol, including rosemary glycophorin together with extract of the mozuku plant, soybean extract, aloe vera extract or ooumegasasou extract.

Patent BR102014029858 suggests a formula for the treatment and styling of hair based on oxidized cysteine, the composition of which comprises oxidized cysteine in the amount of 50% by weight, together with other ingredients such as caprylylglycol in the amount of 0.01 mg, cystene in the amount of 10 mg, hydrolyzed collagen in the amount of 0.5 mg, hydrolyzed elastin in the amount of 0.5 mg, hydrolyzed keratin in the amount of 0.1 mg, Hydroxyethylcellulose in the amount of 0.1 mg, perfume in the 0.3 mg amount, phenoxyethanol in the 0.1 mg amount, and quaternium10 in the amount of 1.0 mg, aminopropylphenyl trimethicone in an amount of 2.5 mg amodimethicone in the amount of 3.0 mg, behentrimonium chloride in the amount of 4.0 mg, caprylyl glycol in the amount of 0.01 mg, centenary chloride in the amount of 1.0 mg, chitosan in the amount of 0.5 mg, ethylhexyl palmitae in the amount of 1.0 MG, hydroxypropyl trimonium chloride 0.8 mg, oxalic acid in the 5, 0 mg and phenoxyethanol in the amount 0.1 mg, trideceth12 in the amount of 1.0 mg and the rest of the composition is water.

Patent JP2854837 proposes a composition for the restoration of black hair, which shows a synergistic activity in the efficacy for the treatment of gray hair and in restoring black hair by mixing four types of substances. This black hair restoration solution is obtained by mixing an aloe stock solution (30-70%) prepared by spraying an aloe plant and then filtering the resulting sprayed product with a brown algae plant stock solution (10-40%) obtained spraying a body of algae belonging to the group of brown algae plants and, subsequently, filtering the pulverized material, a stock solution of broccoli (10-40%). It is prepared by pulverizing broccoli and then filtering the pulverized material and honey (5-15%). The result for grey hair is that black hair is revived by applying an appropriate amount of the black hair restoration solution to the scalp. A 6:3:3 ratio of the ingredients is preferred brown seaweed, broccoli solution, honey.

SUMMARY OF THE INVENTION

Therefore, the object of the present invention is an aqueous composition for the treatment of hair that allows to delay and tone grey hair, restoring the natural color of the hair, activating and forming reflections in it, repairing and giving volume with an adequate conjugation of active ingredients, aggressive and in the right amounts, to achieve a surprising revitalizing effect on the hair in a very short treatment time.

Another object of the present invention is a composition for the treatment of hair in the form of a cream that allows to tint the grey hair by restoring the natural color of the hair, activating and forming reflections in it, repairing and giving volume with an adequate conjugation of non-aggressive active principles and in the right amounts, to achieve a surprising revitalizing effect on the hair in a very short treatment time.

The composition that is proposed as the technical object of the invention responds to the result of a meticulous investigation, where the most effective active ingredients and the minimum necessary doses of each of them have been selected to ensure a total revitalization of the hair in a short treatment, returning the natural color to the hair, delaying and toning the grey hair and giving volume for periods of time greater than that achieved with the application of colorants. The conjugation of these principles in minimal proportions, not only reverses the damage caused by the sun and heat on the hair, but derived from its components allows to take advantage of the sun and heat as activators of the positive effects of the composition on the hair, allowing the activation of vitamin D and collagen in the presence of heat and sun; all of this, together with the synergistic effect that occurs between the components of the composition, surprisingly guarantees repaired, nuanced hair with greater volume, and to which its natural color is returned, temporarily disappearing gray hair, without causing negative effects to the hair due to its use at long term.

DETAILED DESCRIPTION OF THE INVENTION

The composition of ingredients that are proposed in this formulation to tone and delay grey hair, revive the color, create natural reflections in the hair, are ingredients already known in their application in cosmetics and in particular in the treatment of hair damaged by the action, systematic of other more aggressive products for bleaching, dyeing or straightening. However, in the analysis of the state of the art in general on hair treatment products, a similar composition was not found from the quantitative and qualitative point of view of its ingredients, much less has it been found that in the state that this technique provides a composition for hair treatment where the sun and heat are the activators of the surprising effects and benefits that the aforementioned composition generates on grey and damaged hair.

Surprisingly, the effects achieved with the application of this formulation allow to obtain improved and revitalized hair in a very short time from its application and the effects of revitalization, restoration of damaged hair, as well as the body, volume, nuance and delay in the appearance of grey hair that acquires after application last longer than that achieved with the individual application of the ingredients that make up the formulation or with the application of the products that are available for the same purposes in the market, the effect It is reactivated every time the hair is exposed to sunlight or, failing that, by applying direct heat for a few minutes with a hand dryer, a surprising, desired and necessary effect.

The natural color of the hair resurfaces with more force, natural reflections are obtained, the grey hair is disappearing, and their appearance is delayed more and more.

In this composition, the sun and heat become allies since the minimum quantities and their relationship between them are activated by the presence of the sun and heat.

With the embodiments shown later in this description, it is possible to verify the effects achieved that are totally superior to those achieved with other products for the same purpose that are currently marketed.

The composition object of the present invention has two expressions or main embodiments, one in the aqueous form of the product and the other in the form of a cream.

The fundamental ingredients that are conjugated in the aqueous composition to revitalize the hair, as well as the functions that they fulfill within said composition are the following:

Collagen: as a restoration and pigmentation agent, it provides firmness, elasticity, body and smoothness to the hair and generates a protective layer of the hair, which is activated in the presence of the sun and heat, allowing the rest of the ingredients to exercise for longer, its functions on the hair.

Hydroxyethylcellulose: as a gelling and thickening agent;

Keratin, as an in-depth hair moisturizing agent, eliminates frizz, and guarantees a better assimilation of the composition through the scalp and through the hair fiber itself;

Aloe vera; hydrates and softens hair;

Citric acid, is used as a pH regulator of the composition, due to its antioxidant properties it also guarantees the potentiation of the revitalizing effect of the hair;

Dextropantothenyl alcohol, is the precursor of vitamin B5, a substance that strengthens the natural protective barrier of dry skin and restores its natural balance. It also stimulates the production of new cells and helps old cells to regenerate;

Sodium Hyaluronate, is used in very low concentrations and ensures with its moisturizing, lubricating and repairing properties the revitalization of the hair in a synergy with the other active ingredients in the composition;

Hydrolyzed Elastin, gives within the composition elasticity and resistance to the hair;

Polyquaternium 7 (Poly (acrylamide-co-diallyldimethylammonium chloride), ensures the required softness in the hair in the proportion used and gives it a natural appearance, also facilitating the styling action, leaving the hair looser and shinier, Preservative agent and water.

The combination of ingredients and the proportions of them by weight of the composition guarantee to tone and delay gray hair, restore the natural color and activate hair growth, thus achieving rapid revitalization, which lasts for several weeks after its application.

The qualitative and quantitative relationship of the aforementioned ingredients in the aqueous composition for hair treatment object of the present invention is as follows:

| | |
|---|---|
| Collagen | 4%-8% |
| Hydroxyethylcellulose | 2%-4%. |
| Polyquaternium 7 | 2%-5%. |
| Aloe vera | 2%-6%. |
| Dextropanthothenyl alcohol | 4%-8%. |
| Elastin Hydrolyzate | 1%-3%. |
| Sodium hyaluronate | 1%-3%. |
| Keratin | 0.8%-3%. |
| Citric acid | 0.2% |
| Preservative Dantogar (1,3-dimethylol-5,5-dimethylhydantoin), Salikat (methylchloroisothiazolinone, benzyl alcohol and methylisothiazolinone), Euxyl K (sorbic acid + potassium sorbate) | 0.2%-0.5%. |
| Fragrance, selected from green apple, lemon lavender, floral | 0.1%-0.5%. |
| Deionized water | 70-89%. |

The way to obtain the aqueous composition formulation is by simply mixing its ingredients.

In the same way, the formulation object of the present invention can be formulated in the form of a cream starting from the same previous ingredients and by adding other ingredients that allow to obtain the form of a cream in the composition.

To obtain the composition in the form of a cream, the formation and mixing of three mixtures is required. The first two mixtures (Mixture 1 and Mixture 2) make it possible to obtain the base of the formulation in the form of a cream and the third mixture (Mixture 3) consists of adding to the base the components described in the formulation of the aqueous composition described above.

The components, quantities by weight and functions of the products that make up the base, the (3) mixtures, which when adding each component of each mixture, said percentages appear in the final mixture, and are described below:

Mix 1:

Varisoft BT (Behentrimonium Chloride) . . . 2%. Quaternary ammonium compound used as a strong hair conditioning agent.

Cethyl Alcohol . . . 7%. It acts as a thickening and emulsifying agent to avoid separation of the ingredients of the composition.

Alcohol Myristic . . . 2%. It acts as an emulsifier, emollient.

Solid Vaseline . . . 4%. It acts as a base to make the cream.

Isopropyl Myristate . . . 2%. It acts as an emollient and favors the penetration of active principles present in the composition.

Lauric Alcohol . . . 1.5%. Acts as a viscosity controlling agent

Mix 2:

Propylene glycol . . . 5%. Helps retain its moisture content in the formulation.

Dehyquart A (Cetrimonium chloride) . . . 5%. It acts as a conditioner and has a positive influence on wet and dry combability.

Treated water . . . 57%.

Mix 3:

After obtaining the base (Mix 1+Mix 2), mix 3 consists of the components already described and mentioned to obtain the aqueous composition.

For the conformation of the composition in the form of cream, first Mix 1 and Mix 2 are obtained separately, both mixtures are brought to a temperature of 70 degrees until dissolution and then 1 and 2 are mixed to finally add the components of the mixture, formula corresponding to the aqueous composition already described.

Either of the two formulations (aqueous or cream) are applied directly to clean hair, left to act for 10 to 15 minutes, subjected to heat to dry, returning the hair to its natural color. These formulations have the property of repairing, shading, activating, and giving volume to the hair while returning its natural color, delaying the appearance of grey hair for periods of time greater than that achieved with the application of dyes. Additionally, the hiding effect of grey hair can be reactivated when the hair is again subjected to the action of heat, for example from a hair dryer without the need to reapply the composition object of the present invention, which allows the protection of the hair and the concealment of grey hair for longer and at a lower cost.

The invention claimed is:

1. An aqueous composition to delay and tone a grey hair, restoring natural color of the hair creating natural reflections, giving volume, fixing the natural color of the hair, the comprising by weight percent of the composition:
    collagen 4%-8%,
    hydroxyethylcellulose 2%-4%,
    polyquaternium 7 2%-5%,
    aloe vera 2%-6%,
    dextropantothenyl Alcohol 4%-8%,
    elastin hydrolyzate 1%-3%,
    sodium hyaluronate 1%-3%,
    keratin 0.8%-3%,
    citric acid 0.2%,
    preservative 0.2%-0.5%,
    fragrance 0.1%-0.5%, and
    deionized water of 70-89%;
    wherein the composition is activated by heat or sun light.

2. The composition according to claim 1, wherein the preservative is selected from the group consisting of 1,3-dimethylol-5,5-dimethylhydantoin, methylchloroisothiazolinone+benzyl alcohol+methylisothiazolinone, and sorbic acid+potassium sorbate.

3. The composition according to claim 1, wherein the fragrance is selected from the group consisting of green apple, lemon, lavender, and flower essence.

4. A cream composition comprising:
    a first mixture comprising by weight of the composition: behentrimonium chloride 2%, cetyl alcohol 7%, myristic alcohol 2%, vaseline solid 4%, isopropyl myristate 2% and lauric alcohol 1.5%;
    a second mixture comprising by weight of the composition: propylene glycol 5%, cetrimonium chloride 5% and water 57%; and
    a third mixture comprising by weight of the composition: collagen 4-8%, hydroxyethylcellulose 2-4%, polyquaternium 7 2-5%, aloe vera 2-6%, dextropantothenyl alcohol 4-8%, elastin hydrolysate 1-3%, sodium hyaluronate 1-3%, keratin 0.8-3%, citric acid 0.2% preservative 0.2-0.5% and fragrance 0.1-0.5%;

wherein the combined mixtures are in the form of a cream.

5. A method of preparing a cream composition comprising:
   combining a first mixture comprising by weight of the composition: 2% behentrimonium chloride, cetyl alcohol 7%, myristic alcohol 2%, vaseline solid 4%, isopropyl myristate 2% and lauric alcohol 1.5%; and a second mixture comprising by weight of the composition: propylene glycol 5%, cetrimonium chloride 5% and water 57%;
   heating the combined first mixture and second mixtures until dissolved;
   subsequently adding a third mixture comprising by weight of the composition: collagen 4-8%, hydroxyethylcellulose 2-4%, polyquaternium 7 2-5%, aloe vera 2-6%, dextropantothenyl alcohol 4-8%, elastin hydrolysate 1-3%, sodium hyaluronate 1-3%, keratin 0.8-3%, citric acid 0.2% preservative 0.2-0.5% and fragrance 0.1-0.5% to the dissolved mixture; and
   mixing to obtain the cream composition.

* * * * *